United States Patent [19]
Sun

[11] Patent Number: 6,096,368
[45] Date of Patent: Aug. 1, 2000

[54] BEAD TRANSPORTER CHUCKS USING REPULSIVE FIELD GUIDANCE AND METHOD

[75] Inventor: Hoi Cheong Sun, Monmouth Junction, N.J.

[73] Assignee: Delsys Pharmaceutical Corporation

[21] Appl. No.: 09/026,303

[22] Filed: Feb. 19, 1998

[51] Int. Cl.[7] .............................. A61J 3/00; B05D 1/22; B05D 1/04; B23B 5/22; C25D 17/04
[52] U.S. Cl. ..................... 427/2.14; 279/128; 427/458; 427/475; 427/485; 204/297 M
[58] Field of Search ................. 204/297 M, 297 R; 279/128; 118/DIG. 2; 427/458, 2.14, 475, 485

[56] References Cited

U.S. PATENT DOCUMENTS

| | | | |
|---|---|---|---|
| 5,653,859 | 8/1997 | Parton et al. ............................ | 204/450 |
| 5,728,532 | 3/1998 | Ackley ........................................ | 435/6 |
| 5,788,814 | 8/1998 | Sun et al. ........................ | 204/297 M X |
| 5,846,595 | 12/1998 | Sun et al. ................................ | 427/2.14 |
| 5,858,099 | 1/1999 | Sun et al. ................................ | 118/621 |

FOREIGN PATENT DOCUMENTS

| | | |
|---|---|---|
| 0 403 263 A2 | 12/1990 | European Pat. Off. . |
| 0 815 942 A1 | 1/1998 | European Pat. Off. . |
| 2 749 393 A1 | 12/1997 | France . |
| WO 97/38480 | 10/1997 | WIPO . |

*Primary Examiner*—Donald R. Valentine
*Attorney, Agent, or Firm*—Dechert Price & Rhoads

[57] ABSTRACT

Bead transporter chucks for selective pick up and discharging of polymer beads for chemical synthesis or analysis, whereby repulsive field conductors are arranged around bead electrodes used for selectively attracting and retaining beads. Problems of bead control are addressed by adding repulsive fields to help guide and direct beads to desired or designated bead collection zones. The repulsive electrodes create non-uniform electric fields that control, focus, and deflect charged beads in the vicinity of the bead collection zone, helping prevent multiple bead retention at intended bead collection zones. For better bead control, and allowing manipulation of beads with higher charge/mass ratios, dielectric material may be positioned around the bead electrode and between the bead electrode and the repulsive field conductor. Multiple bead electrodes may be provided to form two or more bead collection zones, and these may selectively addressed and controlled (e.g, x-y addressing) for individual and selective control of the bead collection zones. Methods and applied voltages are given for using the bead transporter chuck to transport and dispense beads.

19 Claims, 3 Drawing Sheets

BEAD TRANSPORTER CHUCKS USING REPULSIVE FIELD GUIDANCE AND METHOD

The present invention is directed to devices for electrostatically picking up and dispensing beads in a spatially resolved manner. Specifically, this disclosure describes improved electrode configurations and operation techniques for electrostatic bead transporter chucks that pick up, manipulate, transport, and then discharge or place beads or object, for use in creating pharmaceutical or chemical compositions, or in performing assays or chemical analysis.

Bead transporter chucks act as clamps to hold or retain beads. Bead transporter chucks provide superior performance for manipulating synthetic beads having typical diameters of 100–300 microns in chemical synthesis, such as combinatorial chemistry for solid phase synthesis, or in an assay using PCR (polymerase chain reaction), or other processes. In combinatorial chemistry, a multi-well array such as a microtiter plate allows screening or synthesis of many compounds simultaneously.

For example, bead transporter chucks allow deposition of beads on an array in a manner that is faster and more reliable than by the use of micropipettes, which can be inefficient, tedious, and time consuming. Another application for bead transporter chucks is synthesis of pharmaceutical compositions, especially when used to combine compounds to form compositions to be packaged into administration forms for humans or animals.

Beads containing one or more active ingredients may be deposited onto well known carriers or substrates to make pharmaceutical dosage forms. Such beads may take the form, for example, of [1] a powder, such as dry micronized forms made by air jet milling processes, where overall particle dimensions can be, for example, in the 1 to 10 micron range useful for dry powder respiratory administration of medicaments, with 4–8 microns preferred; [2] microspheres; [3] extremely small structures, including fullerenes, and chelates; or [4] liposomes and fatty droplets formed from lipids or cell membranes.

The use of bead transporter chucks provides a customized and precise method for formulating drug compositions. The transporter can be used to merge adjacent substrates carrying active ingredient to form multidosage packs, in which dosage can decrease or increase from one individual unit to the next, as in hormone-based (e.g., birth control) drugs or antibiotic remedies. Using an electrostatic bead transporter chuck, dosages may be easily established or determined by the number and/or type of beads dispensed onto each pharmaceutical carrier. Using bead transporter chucks to place active ingredients into pharmaceutical compositions can give high repeatability and is also advantageous when the active ingredients are not compatible, such as when the active ingredient is poorly soluble with the carrier, or where a formulation carrier negatively affects the bioavailability of the active ingredient.

Although emphasis is placed in this disclosure on electrostatic bead transporter chucks using electric fields for bead retention and/or release, the teachings given here may be applied to chucks using other phenomena, such as the use of compressed gas or vacuum, or electrically/chemically switchable adhesives, in controlling beads. Electrostatic holding mechanisms, however, are far more benign to delicate bead structures than traditional mechanical techniques, particularly when manipulating biologically active compounds where crushing, contamination, or oxidative damage must be minimized or eliminated.

The present invention may also be used in conjunction with acoustic bead dispensers, where acoustic energy, provided by a speaker or piezoelectric device, is used to great advantage in bead control, that is, propelling and/or tribocharging beads prior to, and especially during, electrostatic manipulation. Tribocharging beads, as known in the art, and described below, is more efficient and less damaging to the beads than corona or plasma charging, which typically requires high applied voltages of around 5 kV. Often, the sonically vibrating membrane used in such an acoustic bead dispenser may itself be used to tribocharge the particles, eliminating the need to charge the beads prior to their entry into the acoustic dispenser. The use of acoustic dispensers allows polarity discrimination of beads, where wrongly charged beads are discouraged from being retained by the bead transporter chuck.

In the course of bead manipulation and control, particularly when using electric fields and polarization to guide beads, certain problems arise and certain requirements have become apparent.

First, it is desirable to have one, and only one bead to be attracted, transported, and discharged for each bead transporter chuck, or for each well, pixel, or individual spatial element of the bead transporter chuck. This is especially true for certain embodiments, where each pixel may be considered a tiny bead transporter chuck that is selectively and independently controlled, such as planar chucks having individually addressable x and y coordinates. This includes individually addressable pixels for different (multiple) bead types.

Second, beads manipulated by the bead transporter chuck must be easily and controllably releasable, with wrongly charged beads (objects or beads having a charge of the opposite polarity desired) not occupying bead retaining or collecting zones on the bead transporter chuck.

Third, the bead transporter chuck should function well for a wide range of bead diameters, including beads with general dimensions of 100 microns and up, and especially porous or hollow beads that have high charge/mass ratios.

Fourth, bead transporter chuck components should be durable, re-usable, and preferably have good ease-of-use, including having selectively or wholly transparent elements for easy movement and alignment of the chuck with intended targets or carriers.

Methods for use of bead transporter chucks and acoustic bead dispensers are set fort in Sun, "Chucks and Methods for Positioning Multiple Objects on a Substrate," U.S. Pat. No. 5,788,814, issued Aug. 4, 1998; Sun et al., "Electrostatic Chucks," U.S. Pat. No. 5,858,099, issued Jan. 12, 1999; Pletcher et al., "Methods and Apparatus for Electronically Depositing a Medicament Powder Upon Predefined Regions of a Substrate," and continuation-in-part thereof U.S. Pat. No. U.S. Pat. No. 6,007,630, issued Dec. 28, 1999; and Sun et al., "Acoustic Dispenser," U.S. Pat. No. 5,735,302; issued May 19, 1998.

Bead transporter chuck designs that use simple attraction electrodes to pick up and discharge beads can, under certain conditions, encounter serious problems with bead density and control. One problem encountered is that many more beads than desired are attracted to intended bead collection zones. During synthesis or analysis, instead of retaining one and only one bead per bead collection zone, multiple beads or even whole clumps of beads are attracted to bead collection zones when using typical or desired attracting voltages needed for efficient manipulation of the beads. Alternatively, in seeking to avoid this bead clumping by reducing the applied (attraction) voltage, the attraction field is then not sufficient to cause beads to deposit in the required manner, i.e., one bead per hold, without either having beads attracted to unintended or wrong locations on the bead transporter chuck, or having wrongly charged beads attracted to the bead transporter chuck.

It is important to keep in mind that particle charging—whether by triboelectric and contact transfer, corona charging, or thermionic and field emission charging—occurs essentially at the particle surfaces. These surface effects are well known, and are aided by electric polarization, that is, induced surface charge in response to an applied electric field. Polarization is ubiquitous in nature. A charged rod, for example, will attract uncharged bits of paper, etc.

However, the problem in bead pickup and dispensing is one of balancing electrical fields, and making non-uniform fields that will guide beads singly to intended bead collection zones. In attracting and manipulating beads, image charges, and electric polarization play a role.

In particular, it is well known that dielectrics, such as polymer beads, that are placed in a uniform electric field will not experience a net force. In an essentially uniform field, such as between two large charged plates, the induced surface charge or charge shifting that results from electric polarization does not yield any significant net force on a neutral or uncharged object. To include the action of neutral beads, and for maximum bead guidance and attraction, it is desired to have non-uniform fields whose fields lines converge or diverge. If one uses uniform electric fields, the applied voltages required to attract and retain beads causes too many beads to be retained at bead collection zones.

To illustrate this, Dupont® Kapton® polyimide film with a copper exterior metallization may be used in a closed container to attract beads using a simple uniform electric field. A simple bead transporter chuck comprising a planar electrode, copper on Kapton®, forms the top of the container. The copper/Kapton® planar electrode of the chuck may have bead holes or apertures to act as bead collection zones into which the attracted beads may nestle. A voltage of 3000 volts is applied between [1] the planar copper/Kapton® electrode; and [2] a conductive base plate or mesh at the bottom of the container. After precharging 105 mg of 280 micron diameter polymer beads inside a precharging chamber using methods known in the art, the polymer beads are introduced into the closed container. It is then found that with the applied voltage of 3000 volts that the highest distance D that may be used to reliably attract beads is about one inch (2.54 cm) between the bead contact surface of the chuck and the conductive base plate or mesh. We can calculate roughly the minimum charge/mass ratio that a bead must possess to be raised and attracted to the bead holes on the chuck. The electrical force $F_{elec}$ generated in the uniform field E inside the container must be equal to or greater than the force $F_{grav}$ of gravity:

$$F_{elec}=Eq>F_{grav}=mg \quad (1)$$

and the result for this example is that the minimum charge/mass for beads to be manipulated by the chuck is about 83 nC/g. However, a problem arises: even using the maximum distance D to let gravity act in minimizing bead density at the bead collection zones, many beads per bead hole can nonetheless be found there.

It is therefore important to have a better form of bead guidance and control when loading beads from any dispensing device(s) to the bead transporter chuck. It is also highly desirable that the electric field used for lifting desired beads between the bead transporter chuck and the bead dispensing device(s) not be large enough to raise or attract most of the available beads from the dispenser to the bead transporter chuck. However, at the same time, the electric field around bead collection zones (where beads should be selectively retained, singly) should be large enough locally to raise a small portion of the available beads from the dispenser to the bead transporter chuck. Ideally, the field around a bead collection zone should be weakened substantially when a bead is captured or retained there. The higher the charge/mass ratio of the beads (such as with certain tribo-charged porous or hollow beads), the greater these problems of control can become.

SUMMARY OF THE INVENTION

These problems of bead control are addressed in this invention by adding repulsive fields to help guide and direct beads to desired or designated bead collection zones. The repulsive electrodes, together with other field-generating features, can create non-uniform electric fields that control, focus, and deflect charged beads in the vicinity of the bead collection zone, and greatly narrow the opportunity for multiple bead retention at intended bead collection zones.

For convenience in describing the bead transporter chuck, a convention will be adopted that speaks of the chuck "picking up" beads onto the bead contact surface on the underside of the chuck. This convention is adopted merely to facilitate description, so that those of ordinary skill should understand that other orientations will be utilized.

In one embodiment, a bead transporter chuck for attracting beads to a bead collection zone on a bead contact surface is disclosed whereby one or more bead electrodes are provided for selectively establishing a bead attracting field to a bead collection zone; and a repulsive field conductor is provided with the repulsive field conductor shaped and configured in such a manner so that when an appropriate potential is applied to it, the beads, are influenced by it and guided to selective retention by the bead electrode to the designated bead collection zones. Typically, the repulsive electrode is arrayed sufficiently around the bead electrode to apply a field that can influence beads approaching the bead contact surface from any direction. In illustrative embodiments, the repulsive field conductor surrounds the bead electrode.

Optionally, one may add to the bead transporter chuck a shield electrode which is shaped and configured to allow beads to be influenced by the bead electrode and by the repulsive field conductor, but allowing a shaping and narrowing of prevailing electric fields to aid in bead control.

For better bead control, and allowing manipulation of beads with higher charge/mass ratios, the bead contact surface may also comprise, with or without the shield electrode, dielectric material positioned around the bead electrode and between the bead electrode and the repulsive field conductor.

The bead electrode can be positioned for exposure to the bead contact surface, or can be shielded by the dielectric material. Multiple bead electrodes can be provided to form two or more bead collection zones, and these can selectively addressed and controlled (e.g, x-y addressing) for individual and selective control of the bead collection zones.

Also disclosed are methods for using the bead transporter chuck to transport and dispense beads. These methods comprise applying a first potential to the bead electrode of the bead transporter chuck to create a bead attracting field; and attracting and retaining a bead to the bead collection zone. A second potential of opposite polarity to the first potential may also be applied to the repulsive field conductor to help guide beads to the bead collection zone. If using a shield electrode, a bias between that of the bead electrode and that of the repulsive field conductor is preferably used.

To discharge beads, methods provided include reducing the first potential applied to the bead electrode, thereby reducing the bead attracting field sufficiently so as to discharge a bead from the bead collection zone to a desired location. When discharging beads, one may align the bead transporter chuck with the desired location prior to discharge.

When discharging beads, one may also reduce or reverse the second potential to aid in bead placement and stability. When using a shield electrode on the bead contact surface, discharge steps may include grounding or biasing to repulse beads.

DEFINITIONS

The following definitions shall be employed throughout:

"Bead" or "beads" shall refer to any material thing such as a particle, object, tablet or receptacle, capable of being manipulated. This shall include spheres or beads made from polymer and reactive polymer masses, such as styrene-based polymers used in the Merrifield type of solid-phase synthesis.

"Bead collecting zones" shall include all surfaces of the bead contact surface at which bead attracting fields generated by bead electrodes attract and favor retention of a bead. In preferred embodiments of the invention, the bead collecting zones are found at holes or apertures formed on the bead contact surface, and these holes can be sized to favor retention of beads of a selected size range or shape.

"Bead contact surface" shall include all surfaces of the bead transporter chuck that are accessible to bombardment, contact or exposure to beads, regardless of whether such access is physically encouraged or discouraged.

"Bead electrode" shall connote any electrode meant to attract and retain materials things such as beads, objects, or particles. It can optionally comprise a hole or aperture into which a bead or object can be selectively retained and/or viewed. Upon reducing of the electrical potential applied to it, a bead electrode can selectively allow discharge or release of any bead or beads retained.

"Conductor" and "electrode" shall include surfaces or sets of surfaces, continuous or non-continuous, that are capable of carrying electric current.

"Dielectric" shall refer to any dielectric material, such as electric insulators in which an electric field can be sustained with a minimum power input; the term is applied generally such that solid metals, if manipulated to meet this definition, for example with a radio frequency applied voltage, can be considered dielectrics. This dielectric material need not be solid (e.g., it may be hollow) and it can be made up of substructures or different constituent dielectric subparts or material types.

"Reducing," such as in the context of reducing applied potentials to bead electrodes to allow bead discharge, shall include reduction and reversal of polarity of the applied potential, such as going from +500 V to −500 V or vice versa.

"Repulsive field conductors" shall refer to electrodes on the bead transporter chuck that function to generate electrical fields that discourage beads from being attracted or retained, at locations other than bead collection zones. Repulsive field conductors need not be explicitly repulsive, that is, have the same charge polarity as the beads to be picked up and later discharged. For example, a repulsive field conductor can be held at ground potential, with the resultant deflection of prevailing attraction field lines $E_a$ and polarization and discrimination field lines $E_p$ providing field guidance to discourage bead retention outside bead collection zones.

"Shield electrodes" refers to electrodes that are used to shield (at least partially) a charged bead that is approaching or proximate to a bead collection zone from being influenced by a repulsive field generated by a repulsive field conductor, and/or to define and shape (narrow) the local electric attraction field to encourage bead retention only in the intended bead collection zone.

Regarding electrode orientations, and surrounding dielectrics, the invention is sometimes defined using the terms "around," "between," and "surrounding," such as where a repulsive field conductor is formed around, or surrounds, a corresponding bead electrode. When electrodes, conductors, or dielectrics are found on different levels or layers of the bead transporter chuck, "around" and "surround" are to be interpreted in view of the areas of the bead contact surface to which the electrode or structure in question will map to by projecting each point to the nearest point on the bead contact surface.

It is also important to note that although the term electrostatic is used throughout this disclosure, no limitation is meant or intended in terms of time variations of charge on electrodes and conductors used in the present invention. Electrical currents can and will flow in the course of using the bead transporter chucks as described, in order to apply and remove electric charge as required. Potentials refer to electric potentials or applied voltages.

DETAILED DESCRIPTION OF THE INVENTION

Figure 1:
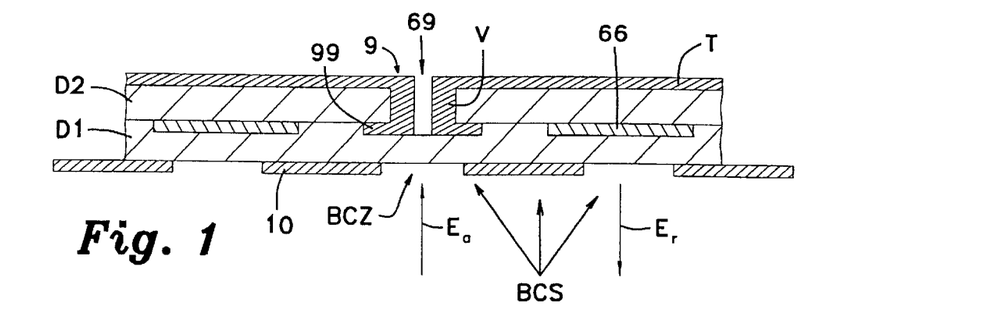
FIG. 1 shows a cross-sectional view of a portion of one bead transporter chuck according to the present invention, illustrating structures that form one pixel or bead collection zone.

Referring to FIG. 1, a cross-sectional view of a portion of one bead transporter chuck according to the present invention is shown. Structures needed for a single bead collection zone are shown. The lower portion of this figure shows shield electrode 10 which is applied to one face of first dielectric layer D1 in a parallel plane using any number of techniques known in the art, such as laminating; powder deposition; or thin film deposition, such as magnetron sputtering or electron beam evaporation. Dielectrics that may used include commonly available materials such as Corning Pyrex 7740 glass (high melting point borosilicate glass, Corning Inc, Corning, N.Y.); a typical thickness is 10–20 mils. The shield electrode 10 is formed having apertures (as shown, by way of example). One such aperture allows for establishing a bead collection zone BCZ at the face of first dielectric layer D1. Generally shield electrode 10, and exposed portions of first dielectric layer D1 form a bead contact surface BCS that is accessible to bombardment, contact or exposure to beads inside a bead dispenser or container, not shown. In order to use applied voltages to establish an attraction field $E_a$, as shown pointing to the bead collection zone BCZ, bead electrode 9 is provided.

Electric fields in this and later figures are shown using the standard convention, showing roughly the direction of the force on a positive test charge. However, for actual examples of applied voltages and bead transporter chuck operation in this disclosure, a working convention is adopted that negatively charged beads are to be attracted and later discharged. When manipulating positively charged beads, however, one may simply reverse the applied voltages from those given in the discussion below.

Bead electrode 9 comprises top portion T, via V, and center pad 99. A top portion T of bead electrode 9 is electrically connected to or integral with a center pad 99 by way of via V. The illustrated center pad 99 is in a plane parallel with that of shield electrode 10, but placed on the opposite side, or second face, of first dielectric layer D1. This makes center pad 99 inaccessible to the bead contact surface BCS or the bead collection zone BCZ,. The electric field, however, generated by a potential applied to bead electrode 9 and center pad 99 may emanate through first dielectric layer D1, with the net electric field generated diminished by electric polarization in first dielectric layer D1, depending on its dielectric constant $\epsilon$, which may be anisotropic. See *Classical Electrodynamics 2nd Ed*, John David Jackson, ©1975, John Wiley & Sons, New York.

The aperture in the shield electrode 10 at the bead collection zone BCZ may be sized to favor retention of beads of certain average diameters. A voltage may be applied to bead electrode 9 relative to another surface in the bead dispenser or container to allow attraction of beads to the bead contact surface BCS. Bead electrode 9 may serve to provide an attraction field for a plurality of bead collection zones, but only one bead collection zone is shown here for illustration. To aid in visual confirmation of bead capture at the bead collection zone BCZ, optional bead hole 69 is provided through bead electrode 9, via V, and center pad 99 as shown. For a transparent or translucent dielectric layer D1, bead hole 69 provides a visual or optical monitor sight for whether a bead is retained. This allows for automated verification of bead occupancy in the bead collection zone, using known sensors to determine the hole opacity in terms of percent light transmission. For example, the light transmitted through the bead holes 69 can be optically mapped onto an array detector such as a charge coupled device (CCD), an intensified CCD array, a focal plane array, a photodiode array or photodetector array. The array detector can be, for example, a CCD {such as that available from DALSA, Inc. (Easton Conn.), David Sarnoff Research Center (Princeton, N.J.) or Princeton Instruments (Trenton, N.J.)}, an intensified CCD array {such as that available from Princeton Instruments, Hamamatsu Corp. (Bridgewater, N.J.) or Photometrics Ltd. of Tucson, Ark.}, a focal plane array {such as that available from Scientific Imaging Technologies, Inc. (Beaverton, Oreg.), Eastman Kodak Co., Inc. (Rochester, N.Y.) or David Sarnoff Research Center}, a photodiode array {such as that available from Reticon Corp. (Sunnyvale, Calif.), Sensors Unlimited, Inc. (Princeton, N.J.) or Hamamatsu} or photodetector array {such as that available from FLIR Systems Inc. (Portland, Oreg.), Loral Corp. (New York, N.Y.), or Hughes Electronic Corp. (Los Angeles, Calif.)}.

In order to discourage beads from being attracted or retained at any locations on the bead contact surface BCS other than the intended bead collection zone BCZ, repulsive field Conductor 66 is provided as shown, which is illustrated as in the same plane as, and surrounding, center pad 99 of bead electrode 9. Apertures in shield electrode 10 as shown allow a rejection field $E_r$ from repulsive field conductor 66 to emanate therethrough, after passing through first dielectric layer D1. A optional second dielectric layer D2 is shown between repulsive field conductor 66 and top portion T of bead electrode 9. Via V passes from the top portion T of bead electrode 9 through this second dielectric layer D2 to center pad 99. In lieu of either second dielectric layer D2 or first dielectric layer D1, or both layers, air or the ambient gas or vacuum may be used as a dielectric or insulator. This would expose one or both of repulsive field conductor 66 and bead electrode 9 directly to the bead contact surface. Alternatively, first dielectric layer D1 and second dielectric layer D2 may comprise one single dielectric layer.

Fabrication techniques for forming conductive layers and electrodes in this disclosure may vary considerably, as any known technique satisfying modest electrical and mechanical requirements may be used. Nearly any metal may be used, for example, to form repulsive field conductor 66 and bead electrode 9, which may comprise thermally or electromagnetically deposited metals such as indium tin oxide, brass, platinum, copper, silver, or gold, of any usefull thickness, but preferably about 1000 Angstroms to 10 microns (100,000 Angstroms). The same is true for dielectric layers or laminates—the materials used may be of any type compatible with surrounding electrodes and conductors, and having sufficient dielectric strength to withstand anticipated voltages applied, including ceramic materials; silicon dioxide; alumina; polyimide resins and sheets or other suitable polymers; metallic oxides, such as aluminum oxide and titanium oxide; and titanates of calcium and magnesium.

Conductive vias such as via V may be of any convenient diameter that will carry anticipated electric currents during application and reduction of voltages, preferably greater than 1000 Angstroms, which conveniently for example 50–75 microns in diameter or about 100 microns or more where flexi-curcuit technology is used to fill the vias. Any number of known processes may be used to establish the vias, such as drilling by laser (such as an excimer laser) or etching (such as reactive ion etching including plasma-assisted etching with a direction-providing electrical field), or molding techniques. The use of photoresist masks and related techniques may be used to fill in or complete the conductive portion of a via after drilling. Materials used to complete or form the vias include metals such as spherical gold powder that are suspended in a carrier, such as liquid suspension of resins, solvents and glass, forming a conductive ink. Preferably this preparation is dried and fired after filling to leave a solid plug of conductive material in each via. Regardless of fabrication technique, sizing of via diameters should not be so large as to interfere with other structures such as repulsive field conductor 66 or parts of bead electrode 9.

Figure 2:
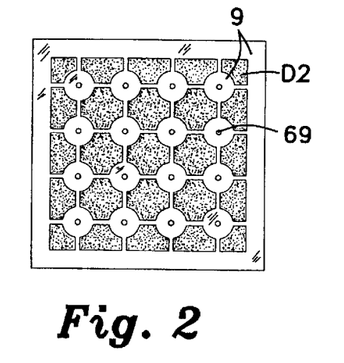
FIG. 2 shows a surface top view of the bead transporter chuck given of FIG. 1, with the bead electrode configured for sixteen pixels or bead collection zones.

Now referring also to FIG. 2, a surface top view of the bead transporter chuck of FIG. 1 is shown, with the bead electrode 9 now shown configured for sixteen pixels or bead collection zones. Each bead collection zone is located in a parallel plane below the plane of bead electrode 9. Each of the sixteen bead holes 69 shown is aligned with one of sixteen bead collection zones, not shown. An observer looking through bead holes 69 could see any retained beads. Spacing of the bead collection zones may vary, depending on the number and size of beads to be manipulated. For example, the entire surface of bead electrode 9 as shown, with all sixteen pixels or bead collection zones, may be a square of sides 49 mm in length; or it may be much smaller, say, 5 mm square, or 1.0 mm square, for manipulating small beads for placement on a smaller substrate, such as a pill or capsule.

Figure 3:
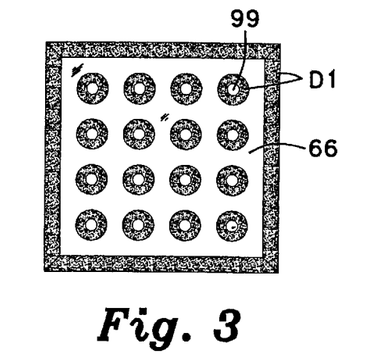
FIG. 3 shows an auxiliary planar view of the bead transporter chuck similar to that shown in FIGS. 1 and 2, with the auxiliary view taken in the plane of the repulsive field conductor.

Referring also to FIG. 3, an auxiliary planar view of a bead transporter chuck similar to that of FIGS. 1 and 2 is shown, with the auxiliary view taken in the plane of the repulsive field conductor 66, and of the center pads 99. This view shows a bead transporter chuck absent bead hole 69 in bead electrode 9. Each center pad 99 coincides with, and provides an attraction field $E_a$ to, a bead collection zone. Notice that aside from openings surrounding and proximate to center pads 99, the repulsive field conductor 66 is continuous, serving to discourage bead retention outside of intended bead collection zones. First dielectric layer D1 is shown in areas not occupied by center pads 99 and repulsive field conductor 66.

Figure 4:
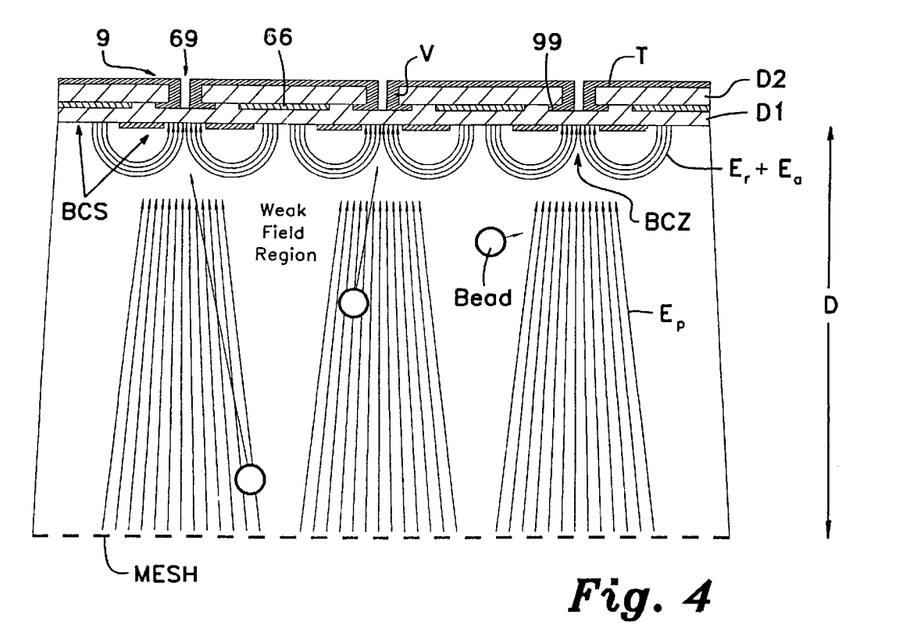
FIG. 4 gives a cross-sectional view similar to that of FIG. 1, where a portion of the bead transporter chuck of FIGS. 1, 2, and 3 is shown, showing structures that form three bead collection zones, and depicting rough electric field lines.

Now referring to FIG. 4, a cross-sectional view similar to that of FIG. 1 is given. A portion of the bead transporter chuck of FIGS. 1, 2, and 3 is shown, showing structures that form three bead collection zones. At the lower end of this figure is a bead dispenser mesh (MESH) shown at a distance D from the bead contact surface BCS. The bead dispenser mesh may be a mesh or a grid through which beads may pass for exposure to the bead transporter chuck. The bead dispenser mesh can also serve as a driving electrode or grid to electrically propel charged beads toward the bead contact surface of the bead transporter chuck. Any number of mesh types may be used, such as a #270 mesh (Newark Wire Cloth Co Newark N.J.) for particles 4–6 microns diameter; or a #200 mesh for particles of greater than 6 microns diameter. The structure shown is as above, with bead electrode 9 electrically connected to three center pads 99 by way of vias V. Repulsive field conductor 66 is again present except in the vicinity of center pads 99.

Rough electric field lines representing $E_r$ emanating from repulsive field conductor 66 and $E_a$ pointing toward center pad 99 of bead electrode 9 are shown, labeled "$E_r+E_a$" and showing field lines explicitly discouraging bead retention on areas of shield electrode or exposed portions of first dielectric layer D1 that are not intended bead collection zones.

Three beads and respective electric field lines are shown for illustration. In practice, one introduces charged beads into the bead dispenser and the space shown between the bead dispenser mesh and the bead transporter chuck with its bead contact surface BCS. For attracting and retaining negatively charged beads, for example, one can apply a negative bias to the bead dispenser mesh (MESH), and a positive bias to the bead electrode 9, while a negative bias applied to repulsive field conductor 66 helps guide beads to their intended destinations at the bead collection zones BCZ.

In one embodiment, the shield electrode 10 is biased between the voltages applied to the bead electrodes 9 and the repulsive field conductors 66. This is conveniently done by connecting the shield electrodes to ground. This enhances user safety at the bead contact surface.

Available bead compositions are well known in the art, and are typically polymer-based, such as divinylbenzene copolymer; polystyrene; polyethylene glycol; or polyethylene glycol graft polystyrene, such as supplied under the trade name PEG-PS by PerSeptive Biosystems of Framingham, Mass.; or cross-linked polyethylene glycol resin, as supplied by Rapp Polymer GmbH of Germany. Beads may be dry, or may have absorbed or adsorbed an aqueous solution, or a fine powder. Beads can also be, for example, dry paint or phosphor particles, or any other powders that can be triboelectrically charged.

Beads may be charged prior to their application to the bead transporter chuck, for example, using plasma charging, or by the use of tribocharging (rubbing or contact charging) as known in the art. Materials that may be used for tribocharging include polytetrafluoroethylene (TEFLON®), and polymers of chlorotrifluorethylene, chlorinated propylene, vinyl chloride, chlorinated ether, 4-chlorostyrene, 4-chloro-4-methoxy-styrene, sulfone, epichlorhydrin, styrene, ethylene, carbonate, ethylene vinyl acetate, methyl methacrylate, vinyl acetate, vinyl butyral, 2-vinyl pyridine styrene, nylon and ethylene oxide. See, for example, "Triboelectrification of Polymers" in K. C. Frisch and A. Patsis, *Electrical Properties of Polymers* (Technomic Publications, Westport, Conn.), which is hereby incorporated by reference in its entirety. Also see *Handbook of Electrostatic Processes*, Jen-shih Chang, Arnold J. Kelly, and Joseph M. Crowley, eds., Marcel Dekker, Inc., New York, ©1995. For example, polytetrafluoroethylene and polyethylene and other materials that become negatively charged will tend to create a positive charge on the bead or object. Nylon and other materials that become positively charged will tend to create a negative charge on the bead or object. When using mechanical shaking to tribocharge polymer beads, it is preferred that the ratio of the amount or mass of tribocharging material used to charge the beads to the amount or mass of beads is such that their respective total surface areas are about equal.

Generally, there is a discrimination field due to the applied voltage $V_p$ applied between the bead dispenser mesh or driving electrode (MESH) and the bead transporter chuck, generally at the bead electrode 9. For example, bead electrode 9 may be biased at 1800 volts, and the bead dispenser mesh at −1800 volts, for negatively charged beads. This gives an applied voltage $V_p$ of 3600 volts total across distance D. This will function in sorting out beads according to polarity and charge/mass ratio, with beads of a certain charge/mass ratio and correct polarity being encouraged to seat themselves at the bead collection zones.

There is also electric polarization in the beads moving about the space between the bead dispenser mesh and the bead transporter chuck, giving rise to a polarization field. We can sum these fields, and refer to them simply as the polarization and discrimination field, $E_p$, whose field lines are shown, labelled, "$E_p$." The polarization and discrimination field lines $E_p$ tend to point to the center pad 99 of bead electrode 9, leaving a weak field region (Weak Field Region) as shown, at points where the rejection field $E_r$ cancels by superposition much of the field $E_p$.

For a charged bead with a charge/mass ratio q/m, the electrostatic force due to the polarization and discrimination field $E_p$ for improved bead guidance and control should be $$E_p q < m_{bead} g \quad (2)$$

that is, the polarization and discrimination field should not be sufficient in itself to propel beads to bead collection zones. This prevents too many beads from accumulating at the bead collection zones, clumping, etc.

The polarization and discrimination field, $E_p$, is mostly determined by the applied voltage $V_p$ between the bead dispenser mesh and the bead transporter chuck across an overall distance D shown in FIG. 4, $$E_p \approx V_p/D \quad (3)$$

and $E_p$ should therefore be less than that required to lift the beads in the absence of an attraction field from any of the bead electrodes:

$$E_p \leq g/(q/m) \quad (4)$$

Around the bead electrode and associated center pads 99, the rejection field $E_r$ from the repulsive field conductor 66 is small, and so the total net electric field strength is approximately equal to the sum of the polarization and discrimination field $E_p$ and the bead attraction field $E_a$:

$$E_{total} \approx E_p + E_a \quad (5)$$

and for bead capture and control we should have $$(E_p + E_a) q > m_{bead} g \quad (6)$$

only at the bead collection zones adjacent to bead electrode 9 and its associated components.

However, once bead capture by the bead electrode at the bead collection zone has occurred, we should have $$(E_p + E_a) q < m_{bead} g \quad (7)$$

to discourage more than one bead from being retained there. The magnitude of the attraction field $E_a$ preferably drops back considerably after bead capture due to geometric considerations, aided by the fact that electric fields by their nature attenuate in an inverse square relationship.

Naturally, in the bead population inside the bead dispenser there will be variations in both the mass of individual beads and in their respective charges. The charge/mass ratio of the beads is a determining factor in bead guidance and control, and for natural stochastic processes, the bead population distribution P(q/m) will be in the form of a Gaussian distribution or bell curve. In using the bead transporter chuck, one selects a certain minimum or desired (q/m)$_{threshold}$ with $E_p$ and $E_a$ chosen so that $$E_p \leq g/(q/m)_{threshold} \quad (8)$$

but near an active bead electrode (with the attraction potential applied) we should have, at the same time:

$$(E_a + E_p) > g/(q/m)_{threshold} \quad (9)$$

The desired (q/m)$_{threshold}$ can be experimentally determined to avoid having unduly high bead populations seeking and gaining retention at active bead electrodes, since a single bead per bead collection zone is the goal.

The bead transporter chucks according to the examples shown in FIGS. 1–4 reduce greatly the occurrence of wrongly charged beads being retained at bead collection zones. They rely on electrostatic attraction for bead guidance near the bead collection zone, in addition to using the polarization and discrimination field $E_p$. This minimizes the need for acoustic aids in coaxing beads to their intended locations for transport and later discharging. With no physically exposed high voltages from either center pad 99, bead electrode 9 and via V, or repulsive field conductor 66, user safety is enhanced.

For beads having higher charge/mass ratios, such as porous or hollow beads, a stronger attraction field $E_a$ relative to the polarization and discrimination field $E_p$ is needed, along with a less shielded rejection field $E_r$ than before. Beads having higher charge/mass ratios lend to move too quickly, overwhelming the bead contact surface and making the attraction and placement of single beads difficult.

To address this need, another embodiment, an active field chuck, is illustrated by way of example in FIGS. 5, 6, 7, and 8, with similar structures as described above, but using a bead electrode 9 that is exposed to the bead contact surface and eliminating the shield electrode 10.

Referring to FIGS. 5(a)–5(h), cross-sectional views of portions of bead transporter chucks according to the present invention are shown, in a format similar to that of FIG. 1, again with structures shown that form one pixel or bead collection zone. In each of the FIGS. 5(a)–5(h), bead electrode 9 is shown, with top portion T as before, but with longer vias V that extend to to the bead contact surface BCS and form a bead collection zone on or near the BCZ. Dielectric layers D1 and D2 are shown as before, but now there is no shield electrode 10 on the bead contact surface of the bead transporter chuck. As before, repulsive field conductor 66 is continuous and planar, and applied to the other face of dielectric layer first dielectric layer D1. As before, repulsive field conductor 66 also has apertures that allow an attraction field $E_a$ to point toward bead electrode 9 when a voltage is applied. Each bead electrode 9 again comprises a top portion T which may be connected by known means to facilitate electrical addressing. Again, in lieu of either second dielectric layer D2 or first dielectric layer D1, or both layers, air or the ambient gas or vacuum may be used as a dielectric or insulator. This would expose one or both of repulsive field conductor 66 and bead electrode 9 directly to the bead contact surface. Alternatively, first dielectric layer Di and second dielectric layer D2 may comprise one single dielectric layer.

With the bead electrode 9 comprising a lower pad 89 or via V exposed to the bead contact surface, the active electric attraction field generated for a given applied voltage is stronger than for that of the bead transporter chuck of FIGS. 1–4. Also, the exposed bead electrode allows for active charging, where beads momentarily attracted there end up losing or gaining more charge (depending on the polarity of the charged bead) directly to the bead electrode 9. The only drawback is extra safety precautions needed due to exposed high voltage. This safety concern is attenuated since the capacitance of the system will generally minimize risk, and, furthermore, a current limiting resistor placed between the lower pad 89 and the power supply will further minimize any shock hazzard In FIGS. 5(a), 5(c) and 5(e), bead electrode top portion T may be wide relative to the beads to be manipulated, say, ten times the average bead cross sectional area; in other embodiments of FIG. 5, the top portions T are not shown explicitly. In FIGS. 5(a), 5(b), 5(c), and 5(d), each via V of each bead electrode 9 is connected to a lower pad 89 that is exposed to the bead contact surface and forms a bead collection zone. In FIGS. 5(e), 5(f), 5(g), and 5(h), each via V of each bead electrode 9 extends directly to the vicinity of the bead contact surface to form a bead collection zone, without use of a lower pad 89; in FIGS. 5(e) and 5(f), the via V is recessed somewhat from the bead contact surface, forming a nest of sorts for the bead to be attracted and retained. In FIGS. 5(c), 5(d), 5(e), 5(f), 5(g), and 5(h), a bead hole 69 is provided in the central axis of each respective via V to act as a bead capture sight as mentioned above.

Figure 5A:
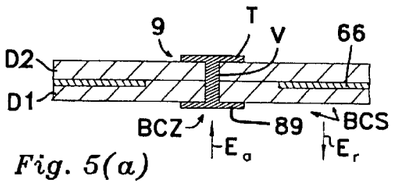
FIGS. 5(a)–5(h) show cross-sectional views of portions of various bead transporter chucks according to the present invention, illustrating structures that can form one pixel or bead collection zone.
Figure 5B:
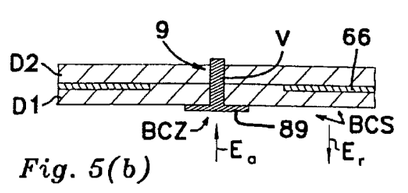
Figure 5C:
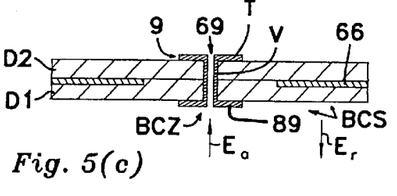
Figure 5D:
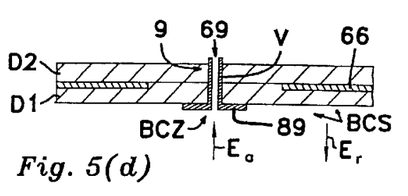
Figure 5E:
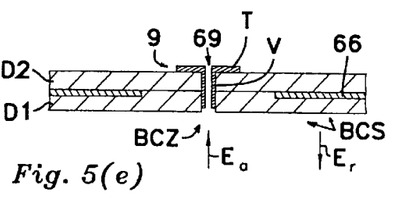
Figure 5F:
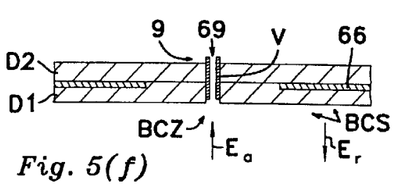
Figure 5G:
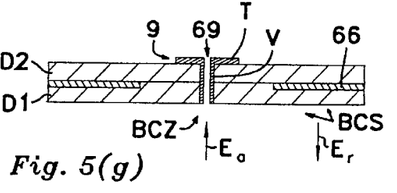
Figure 5H:
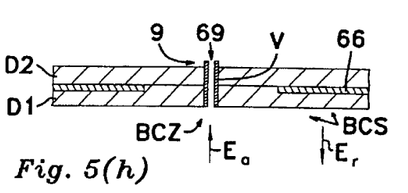
Figure 6:
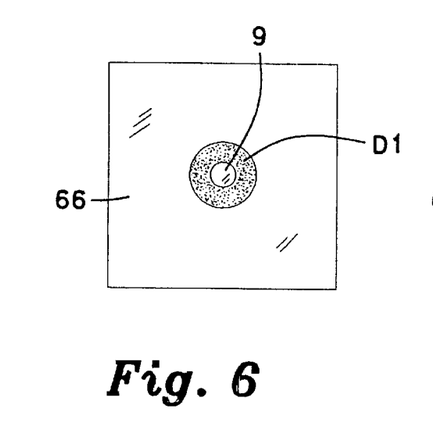
FIG. 6 shows an auxiliary planar view of the bead transporter chuck illustrated by FIGS. 5(a) and 5(b), with the view taken in the plane of the repulsive field conductor, and with only one pixel or bead collection zone shown.

Referring now to FIG. 6, an auxiliary planar view of the bead transporter chuck suggested by FIGS. 5(a) and 5(b) is shown, with the view taken in the plane of the repulsive field conductor 66, and with only one pixel or bead collection zone shown. Via V of bead electrode 9 is shown in the center of the aperture in repulsive field conductor 66. Dielectric material such as first dielectric layer D1 forms the balance of the aperture in repulsive field conductor 66.

Figure 7:
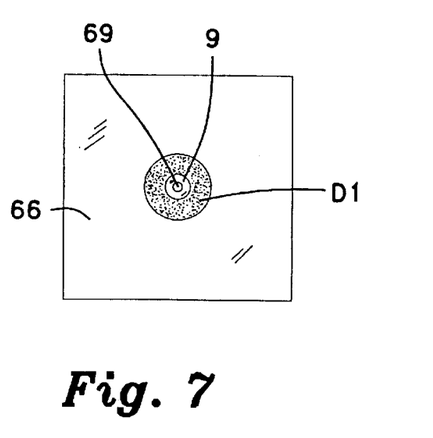
FIG. 7 shows an auxiliary planar view of bead transporter chuck illustrated by FIGS. 5(c), 5(d), 5(e), 5(f), 5(g) and 5(h), with the view taken in the plane of the repulsive field conductor, and with only one pixel or bead collection zone shown.

FIG. 7 shows a similar view to that of FIG. 6, but with the auxiliary planar view taken of the bead transporter chuck suggested by FIGS. 5(c), 5(d), 5(e), 5(f), 5(g) and 5(h). The figure has an identical appearance to that of FIG. 6, except that a bead hole 69 is visible in the center of via V of bead electrode 9.

Figure 8:
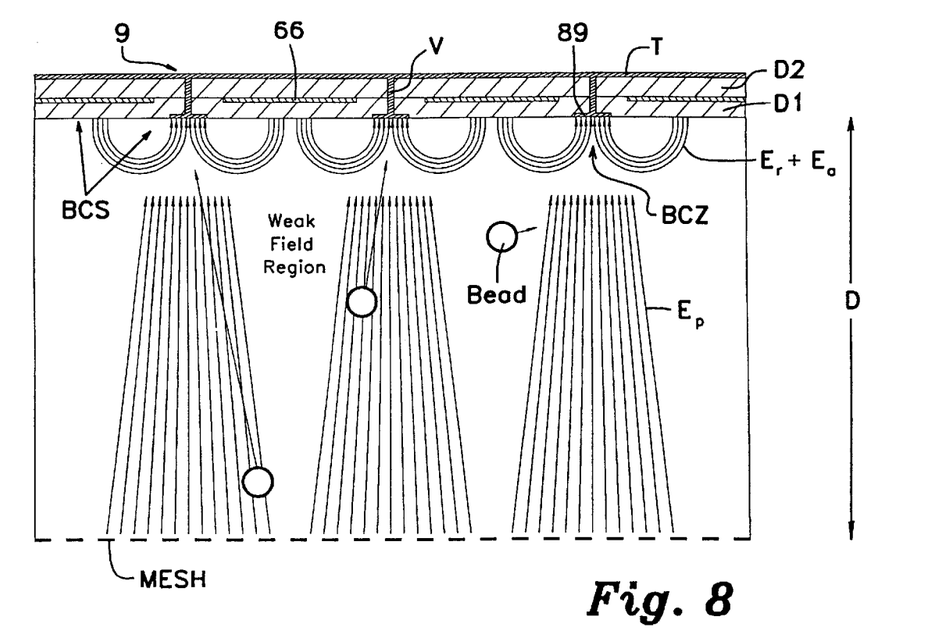
FIG. 8 gives a cross-sectional view of part of a bead transporter chuck structurally similar to those shown in FIGS. 5(a) and 5(b), showing structures that form three bead collection zones, and depicting rough electric field lines.

Referring now to FIG. 8, a cross-sectional view of a portion of a bead transporter chuck structurally similar to those shown in FIG. 5 is given. Structures forming three bead collection zones are shown, using a bead electrode 9 with vias V and lower pads 89 as given in FIGS. 5(a) and 5(b). Rough electric field lines for $E_a$, $E_r$, and $E_p$ are shown as before in above FIG. 4. The polarization and discrimination field lines $E_p$ tend to point to either the lower pad 89 or the via V of bead electrode 9, again leaving a weak field region (Weak Field Region) as shown, at points where the rejection field $E_r$ cancels by superposition much of the field $E_p$.

Overall, bead transporter chucks according to this invention use field guidance so that only around a bead collection zone and bead electrode 9 will the electric fields be strong enough to raise a bead from the bead dispenser or bead dispenser mesh and subsequently guide it toward the bead collection zone and optionally, bead hole 69. Once a bead lands there, it weakens and shields the electric field in the vicinity and no other beads are encouraged to arrive there.

In the course of using the bead transporter chucks of this invention, a number of operating modes may be used. For bead pickup or retention, a bead electrode, either exposed or unexposed to the bead contact surface, is electrically biased to attract beads, while the mesh of the bead dispenser or other conductive surface is biased oppositely. Any number of bead electrodes 9 may be used, and they may be individually and separately connected by known means to facilitate individual and selective addressing in two dimensions. At the same time, one or more repulsive field conductors 66 may be either biased to the same polarity as that of the beads to be attracted, or simply grounded, depending on the sum of the polarization and discrimination field $E_p$ and attraction field $E_a$ desired, as discussed above.

Repulsive field conductors such as shown by repulsive field conductor 66 are electrodes on the bead transporter chuck that function to generate electrical fields, directly or indirectly that discourage or merely deflect beads from being attracted, retained, at locations other than bead collection zones. Repulsive field conductors need not be explicitly repulsive, that is, they do not have to have the same charge polarity as the beads to be picked up and later discharged. For example, as mentioned, the repulsive field conductor may be held at ground potential during bead pickup. This may be aided by the effect of the dielectric surrounding the repulsive field conductor, where net repulsive surface charges will accumulate on the repulsive field conductor in response to a charged bead in the vicinity.

During bead pickup, the shield electrode 10 of the embodiments described in FIGS. 1–4 may be held at ground potential as well. However, it may be biased to a charge polarity similar to that of the desired beads. The shield electrode 10 then becomes a repulsive field conductor. In the embodiments described in FIGS. 1–4, this is tantamount to having an additional repulsive field conductor 66 exposed to the bead contact surface.

However, even when grounded and not acting in an explicitly repulsive manner, shield electrodes are useful, helping to define and shape the attraction field $E_a$ set up by the bead electrodes, particularly because the attraction field would otherwise be shaped instead by any, dielectric material used surrounding the bead electrode, such as first dielectric layers D1. Shield electrode 10 may be allowed to "float," not biased or grounded. Generally however, grounded or not, good results are obtained when the shield electrodes are biased at a voltage between that applied to the bead electrode(s) 9 and that applied to the bead dispenser mesh (MESH).

In one embodiment, the bead transporter chuck described in FIGS. 1–4 may be used. An bead electrode 9 may be fabricated by depositing, using known techniques, such as using a 5000 Angstrom layer of gold (Au) onto the second dielectric layer D2. Alternatively, bead electrode 9 may comprise a 100 Angstrom layer of chromium (Cr) and with a 5000 Angstrom gold (Au) overcoat. Second dielectric layer D2 may be made of Dupont® Kapton® polyimide film (type 300 HN, 3 mil thickness) or on Corning Pyrex7740 glass of 10 mils thickness. Center pads 99 and repulsive field conductor 66 may comprise a 35 micron deposition of copper (Cu) onto first dielectric layer D1. A similar deposition to form the shield electrode 10 may be applied to the opposite face of the first dielectric layer D1, with apertures being about ten times the diameter of the beads to be manipulated.

A bead dispenser container containing this bead transporter chuck is then filled with 270 micron diameter negatively precharged Merrifield beads. A potential of −1800 V is applied to the bead dispenser mesh, +1800 V to the bead electrode 9, and the repulsive field conductor 66 is grounded, set to 0 volts. (This assumes that the desired bead species is negatively charged, or that one is exploiting a polarization-induced negative surface charge on a bead. If a positively charged bead or a positive surface charge is to be used, then these polarities may be reversed.) No wrongly placed beads were observed for adequate distances D between the bead dispenser mesh and the bead transporter chuck, that is D from about ¼' (6 mm) to 1' (25 mm). For smaller distances D, accuracy diminishes.

In another embodiment, the bead transporter chuck as shown in FIGS. 5–8 may be used, using similar fabrication, but with no shield electrode 10 and having exposed bead electrodes 9. A bead dispenser containing this bead transporter chuck is then filled with 270 micron diameter negatively precharged Merrifield beads. Excellent results are again obtained, using lower potentials: a potential of −800 V is applied to the bead dispenser mesh (MESH), +800 V to the bead electrode 9, and the repulsive field conductor 66 is grounded, set to 0 volts. A lower voltage requirement is thus verified for this embodiment In each case, applied voltages cause bead electrode 9 to attract and retain beads, with single beads on each bead collection zone. Beads on the bead transporter chuck are optionally transported to a substrate, microtiter plate, or other destination by moving the entire bead transporter chuck, or alternatively, the target substrate or plate is brought to the chuck. Beads are then released or discharged in a controlled manner when the applied voltages, such as those given above, are reversed or set to zero. Alternatively, for bead release, only the bead electrode 9 may be shorted out or grounded (0 volts), or have an opposite voltage applied. Optionally, when shield electrode 10 is used, it may be biased to be repulsive to beads during bead discharge.

When using bead transporter chucks according to the present invention, the temperature is preferably between −50° C. and 200° C., and more preferably between about 22° C. and 60° C. Relative humidity may be 0–100 percent, so long as condensation does not occur; more preferably the relative humidity is about 30 percent.

Bead holes 69 are typically lined up with, but not necessarily coincident with the bead collection zones. There may be multiple bead collection zones for each independently controlled bead electrode 9. The dielectric layers used allow safety, and electrical isolation between electrodes and conductors. They also reduce fields produced by applied voltages and allow retention of beads containing a higher net charge. In addition, they can also provide structural rigidity and strength to the bead transporter chuck. For preparation of administration forms, precision achieved is high and repeatable, as beads taking the form of microspheres may, in one embodiment, be 1 to 500 microns in diameter, preferably about 50 microns.

By using an appropriate configuration of cyclic or repeating strong repulsive field components in the bead transporter chuck—that is, repulsive field conductors or shield electrodes biased to become repulsive field conductors—beads are field-guided to bead collection zones. The attraction field $E_a$ is substantially reduced once a bead has been picked up, since the bead acts as a shield. Thus, single bead occupancy in each of the individual pixels or elements of the bead collection zone is achieved, with virtually no occurrence of wrongly charged beads at the bead electrodes. An advantage to the use of repulsive field conductors is that they can act as sinks or holding sites for wrongly charged beads that might otherwise make unwanted moves into a bead collection zone.

Bead electrodes 9 may comprise any number of separately addressable pixels or elements in two directions x and y, each having separately controlled bead collection zones. Any number of well known means and structures may be used to facilitate addressing as is known in the electrical and electronic arts, where top portion T previously described in FIGS. 1, 4, 5(*a*)–(*h*), and 8 may comprise a bus or address lead. In this way, combinational synthesis or analysis may be simplified as discussed above. In using the bead transporter chucks, one may expose the bead contact surface of such a chuck to beads selectively apply voltages, such as the voltages given above, for each x-y addressable well, pixel, or individual spatial element of the chuck, to attract and retain beads selectively at each bead collection zone; then release the beads onto a desired destination aligned with the bead transporter chuck by selectively reversing or reducing voltages associated with each bead collection zone as required.

It is also possible that beads attracted by the chuck, especially large diameter beads or objects of large overall size, say 3 mm in diameter, may by known process design become substrates, to be coated with a pharmaceutically active compound. Such beads could include oblong shapes, made of water soluble film, such as hydroxypropyl methyl cellulose resin.

See U.S. Pat. No. 5,714,007, issued Feb. 3, 1998, "Methods and Apparatus for Electronically Depositing a Medicament Powder Upon Predefined Regions of a Substrate," and continuation-in-part thereof U.S. Pat. No. 6,007,630, issued Dec. 28, 1999, which documents are incorporated herein by reference in their entirety.

In this way, electrostatic chucks can be scaled up for large scale continuous manufacturing, such as using a sheet of an edible substrate for use with tablets, for example, or a sheet of an inhaler substrate. For example, hydroxypropyl methyl cellulose can be used, such as Edisol M Film M-900 or EM 1100 available from Polymer Films Inc. (Rockville Conn.). One advantage using bead transporter chucks according to this invention especially the active field embodiments shown in FIGS. 5–8, is that with an exposed bead electrode 9 the chuck can maintain the charge of a pharmaceutical substrate that would otherwise lose its charge. Generally, sizing of bead diameters may range from less than one micron to 1000 microns or larger; 150 microns is fairly typical.

In the claims that follow, terms reciting relative orientation, such as "front," "back," "behind" or "rear" are relative to the bead contact surface (front) of an electrostatic chuck, with the portion oriented behind the side of the bead contact surface on which beads (e.g., particles) are electrostatically attracted being to the rear or back.

Obviously, many modifications and variations of the present invention are possible in light of the above teaching. It is therefore to be understood, that within the scope of the appended claims, the invention may be practiced otherwise than as specifically described or suggested here.

What is claimed is:

1. An electrostatic chuck for attracting particles to one or more bead collection zones on a bead contact surface, comprising:

one or more bead electrodes for connecting to a source of potential for establishing fields for attracting particles to the bead collection zones;

one or more repulsive field conductors shaped and configured so that the projection of the repulsive field conductors onto the bead contact surface surrounds and is separate from such projections of the bead electrodes, the repulsive field conductors adapted to connect to a source of potential effective to discourage particles from approaching an area surrounding the bead collection zones; and dielectric interposed between the bead electrodes and the repulsive field electrode.

2. The electrostatic chuck of claim 1, wherein for at least a portion of the repulsive field conductors that projects to areas on the bead collection surface surrounding projections of the bead electrodes to the bead collection surface, there is no conductor between that portion and the bead collection surface.

3. The electrostatic chuck of claim 2, wherein said bead contact surface comprises one, or more shield electrodes, located in front of the repulsive field conductors, which shield electrodes surround the bead collection zones.

4. The electrostatic chuck of claim 3, further comprising:

one or more power sources or grounds adapted to apply particle attracting first potentials to the bead electrodes, particle repulsing second potentials to the repulsive field conductor, and third potentials—intermediate to the corresponding first potential and the corresponding second potential—to the shield electrodes, wherein the potentials are selected to limit the number of particles approaching portions of the bead contact surface outside the bead collection zones.

5. The electrostatic chuck of one of claims 1, 2 and 3, wherein the electrostatic chuck comprises two or more bead collection zones and a single continuous said repulsive field conductor corresponding to those bead collection zones.

6. The electrostatic chuck of one of claims 1, 2 and 3, wherein the electrostatic chuck comprises sixteen or more bead collection zones and a single continuous said repulsive field conductor corresponding to those bead collection zones.

7. The electrostatic chuck of one of claims 1, 2 and 3, wherein said bead electrodes are positioned for exposure to the bead contact surface.

8. A particle deposition system comprising:
the electrostatic chuck of one of claims 1, 2 and 3; and
a conductive mesh adapted to allow passage through the mesh of the particles, and further adapted to connect to a power source adapted to supply an particle repelling potential to the mesh.

9. The particle deposition system of claim 8, wherein the mesh is adapted to aid in propelling charged particles of 1 to 500 micron diameter toward bead collection surface.

10. The particle deposition system of claim 8, wherein the mesh is adapted to aid in propelling charged particles of 6 micron diameter or less toward bead collection surface.

11. The electrostatic chuck of claim 1, wherein said bead electrodes comprise an upper portion, a via, and a lower pad.

12. The electrostatic chuck of claim 1, wherein said top portion comprises a bus electrode to serve as a connecting bus for the bead electrode.

13. The electrostatic chuck of claim 12, wherein said electrostatic chuck comprises two bead electrodes connected to said bus electrode, forming two bead collection zones.

14. The electrostatic chuck of claim 13, wherein said bus electrode is configured to allow x-y addressing of said bead electrodes to control, individually and selectively, the bead collection zones.

15. A method for using an electrostatic chuck comprising:
(a) providing an electrostatic chuck for attracting particles to one or more bead collection zones on a bead contact surface, comprising:
one or more bead electrodes for connecting to a source of potential for establishing fields for attracting particles to the bead collection zones;
one or more repulsive field conductors shaped and configured so that the projection of the repulsive field conductors onto the bead contact surface surrounds and is separate from such projections of the bead electrodes the repulsive field conductors adapted to connect to a source of potential effective to discourage, particles from approaching an area surrounding the bead collection zones, wherein for at least a portion of the repulsive field conductors that projects to areas on the bead collection surface surrounding projections of the bead electrodes to the bead collection surface, there is no conductor between that portion and the bead collection surface; and
dielectric interposed between the bead electrodes and the repulsive field electrode;
(b) applying a first potential to one of the bead electrodes of the electrostatic chuck to create a article attracting field;

(c) applying a second potential to a said repulsive field conductor surrounding the bead electrode of step (b) of a polarity effective to discourage particles from approaching that repulsive field conductor; and (d) attracting and retaining one or more particles to that bead collection zone or a corresponding location on a substrate positioned on the bead contact surface.

16. The method of claim 15, wherein the provided electrostatic chuck comprises one or more shield electrodes, located in front of the repulsive field conductors, which shield electrodes surround the bead collection zones.

17. The method of one of claims 15 or 16, comprising
(e) applying a pharmaceutically acceptable substrate to the bead contact surface, wherein the particles are attracted to the substrate in step (d) and wherein the particles comprise medicament.

18. A method for using an electrostatic chuck, comprising:
(a) providing an electrostatic chuck for attracting particles to one or more bead collection zones on a bead contact surface, comprising:
one or more bead electrodes for connecting to a source of potential for establishing fields for attracting particles to the bead collection zones;
one or more repulsive field conductors shaped and configured so that the projection of the repulsive field conductors onto the bead contain surface surrounds and is separate from such projections of the bead electrodes, the repulsive field conductors adapted to connect to a source of potential effective to discourage particles from approaching an area surrounding the bead collection zones, wherein for at least a portion of collection surface surrounding projections of the bead electrodes to the bead collection surface, there is no conductor between that portion and the bead collection surface;
dielectric interposed between the bead electrodes and the repulsive field electrode; and
one or more shield electrodes, located in front of the repulsive field conductors, which shield electrodes surround the bead collection zones;
(b) applying a first potential to one of the bead electrodes of the electrostatic chuck to create a particle attracting field;
(c) applying a second potential to a said repulsive field conductor surrounding the bead electrode of step (b) of a polarity effective to discourage particles from approaching that repulsive field conductor;
(d) applying a third potential intermediate between the first and second potentials to a said shield electrode surrounding the bead collection zone for the bead electrode of step (b); and
(e) attracting and retaining one or more particles to that bead collection zone or a corresponding location on a substrate positioned on the bead contact surface.

19. The method of claim 18, comprising
(d) applying a pharmaceutically acceptable substrate to the bead contact surface, wherein the particles are attracted to the substrate in step (d) and wherein the particles comprise medicament.

* * * * *